United States Patent
Ludwig et al.

(10) Patent No.: US 6,942,224 B2
(45) Date of Patent: Sep. 13, 2005

(54) INFLATABLE SEAL

(75) Inventors: Karl F. Ludwig, Girard, PA (US); John C. Houston, Erie, PA (US)

(73) Assignee: Steris Inc., Temecula, CA (US)

( * ) Notice: Subject to any disclaimer, the term of this patent is extended or adjusted under 35 U.S.C. 154(b) by 0 days.

(21) Appl. No.: 10/620,828

(22) Filed: Jul. 16, 2003

(65) Prior Publication Data

US 2005/0012281 A1 Jan. 20, 2005

(51) Int. Cl.[7] ............................................. F16J 15/02
(52) U.S. Cl. ..................... 277/637; 277/628; 277/641; 277/642; 277/644; 277/646
(58) Field of Search ................................. 277/628, 637, 277/641, 642, 644, 646

(56) References Cited

U.S. PATENT DOCUMENTS

| | | | | |
|---|---|---|---|---|
| 3,178,779 A | * | 4/1965 | Clark et al. .................. | 277/646 |
| 3,325,042 A | * | 6/1967 | Brown ........................ | 220/232 |
| 3,815,926 A | * | 6/1974 | Vore ........................... | 277/583 |
| 4,114,901 A | * | 9/1978 | Pot ............................. | 277/646 |
| 4,989,369 A | * | 2/1991 | Maass ........................ | 49/477.1 |

* cited by examiner

*Primary Examiner*—Enoch Peavey
(74) *Attorney, Agent, or Firm*—Kusner & Jaffe; Michael A. Centanni

(57) ABSTRACT

An inflatable seal member for providing a fluid-tight seal. The inflatable seal member is particularly well suited to sealing a processing chamber having pressurized fluids therein. Outward forces (exerted by air pressure) to the inner surfaces of the seal member counteract inward forces (exerted by fluid pressure) to the outer surfaces of the seal member.

11 Claims, 4 Drawing Sheets

INFLATABLE SEAL

FIELD OF THE INVENTION

The present invention relates to sealing apparatus, and more particularly to an inflatable seal member.

BACKGROUND OF THE INVENTION

Seals are used in a wide variety of apparatus to provide a barrier that prevents the transmission of fluids thereacross. In the case of an automated reprocessor, a seal is provided to prevent the escape of anti-microbial fluids (e.g., disinfectants, sterilants and the like) from a processing chamber. Automated reprocessors are used for microbial decontamination (e.g., sterilization, disinfection, sanitation, and the like) of articles, including, but not limited to, medical devices, pharmaceutical devices, dental devices, mortuary devices and the like. An automated reprocessor decontaminates the articles by exposing them to an anti-microbial fluid, such as liquid peracetic acid, or other oxidants. A door or lid provides access into a processing chamber, wherein the articles to be decontaminated are exposed to an anti-microbial fluid. Typically, a rigid seal is provided between the door or lid, and a housing to prevent the escape of fluids from the processing chamber.

The present invention provides an improved seal member for providing a fluid-tight seal around the processing chamber used to decontaminate articles.

SUMMARY OF THE INVENTION

In accordance with the present invention, there is provided in a device having a chamber defined by a lid and a cavity, a seal member for sealing the chamber comprising: (1) a base portion adapted to be received within a slot formed in the lid; (2) a seal portion having a substantially concave inner surface and a substantially convex outer surface; and (3) first and second flexible side walls, each of said first and second flexible side walls connected between the base portion and the seal portion, wherein said base portion, seal portion, and first and second flexible side walls define an inflatable inner cavity.

In accordance with another aspect of the present invention, there is provided a method for operating an inflatable seal member having an inner cavity, in a device having a chamber defined by a lid and a cavity, the method comprising the steps of: (1) moving the lid from an open position to a closed position to enclose the cavity, wherein said inflatable seal member has an uninflated normal configuration; (2) locking the lid in the closed position; and (3) inflating the inflatable seal member, wherein said inflatable seal member assumes an inflated configuration.

An advantage of the present invention is the provision of a seal member that inflates to provide a fluid-tight seal.

Another advantage of the present invention is the provision of a seal member that can maintain a seal under high pressure conditions.

A still further advantage of the present invention is the provision of a seal member that provides an improved seal for enclosing a chamber.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF A PREFERRED EMBODIMENT

While the present invention is described herein with particular reference to an automated reprocessor, this is not intended to limit the scope of the present invention. In this regard, it is contemplated that the present invention finds utility in a wide range of apparatus requiring a seal, and especially those apparatus requiring a fluid-tight seal.

Figure 1:
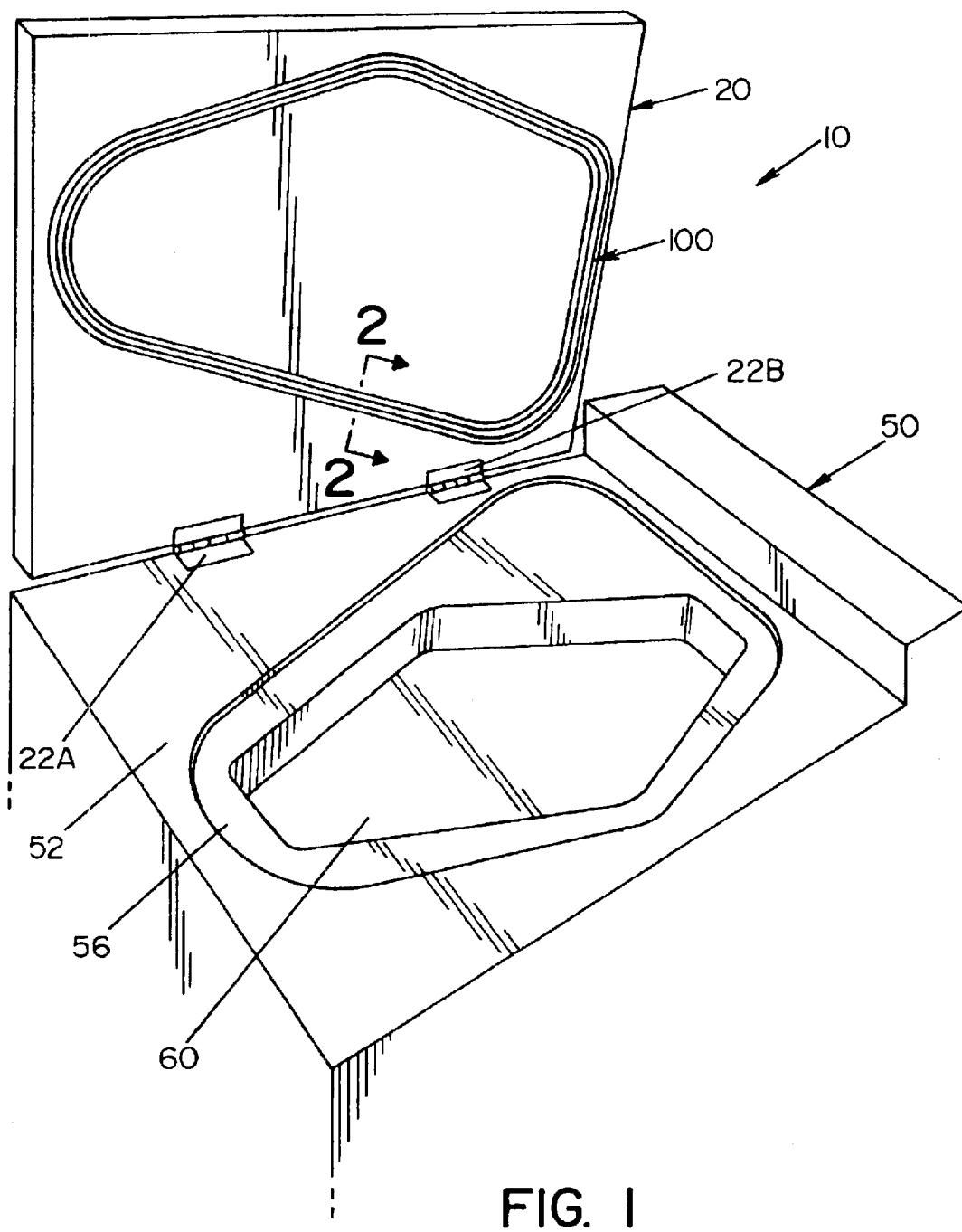
FIG. 1 is a perspective view of the top portion of an automated reprocessor having an inflatable seal member located in a lid, according to a preferred embodiment of the present invention.

Referring now to the drawings wherein the showings are for the purposes of illustrating a preferred embodiment of the invention only and not for purposes of limiting same, FIG. 1 shows the top portion of an automated reprocessor 10 for decontaminating articles. Automated reprocessor 10 is generally comprised of a generally planar lid 20, and a housing 50, only a portion of which is shown. In a preferred embodiment, lid 20 is attached to housing 50 by hinges 22A, 22B. A seal member 100 is mounted to lid 20 to form a seal assembly 90 (FIGS. 2–4), as will be described in detail below.

Figure 2:
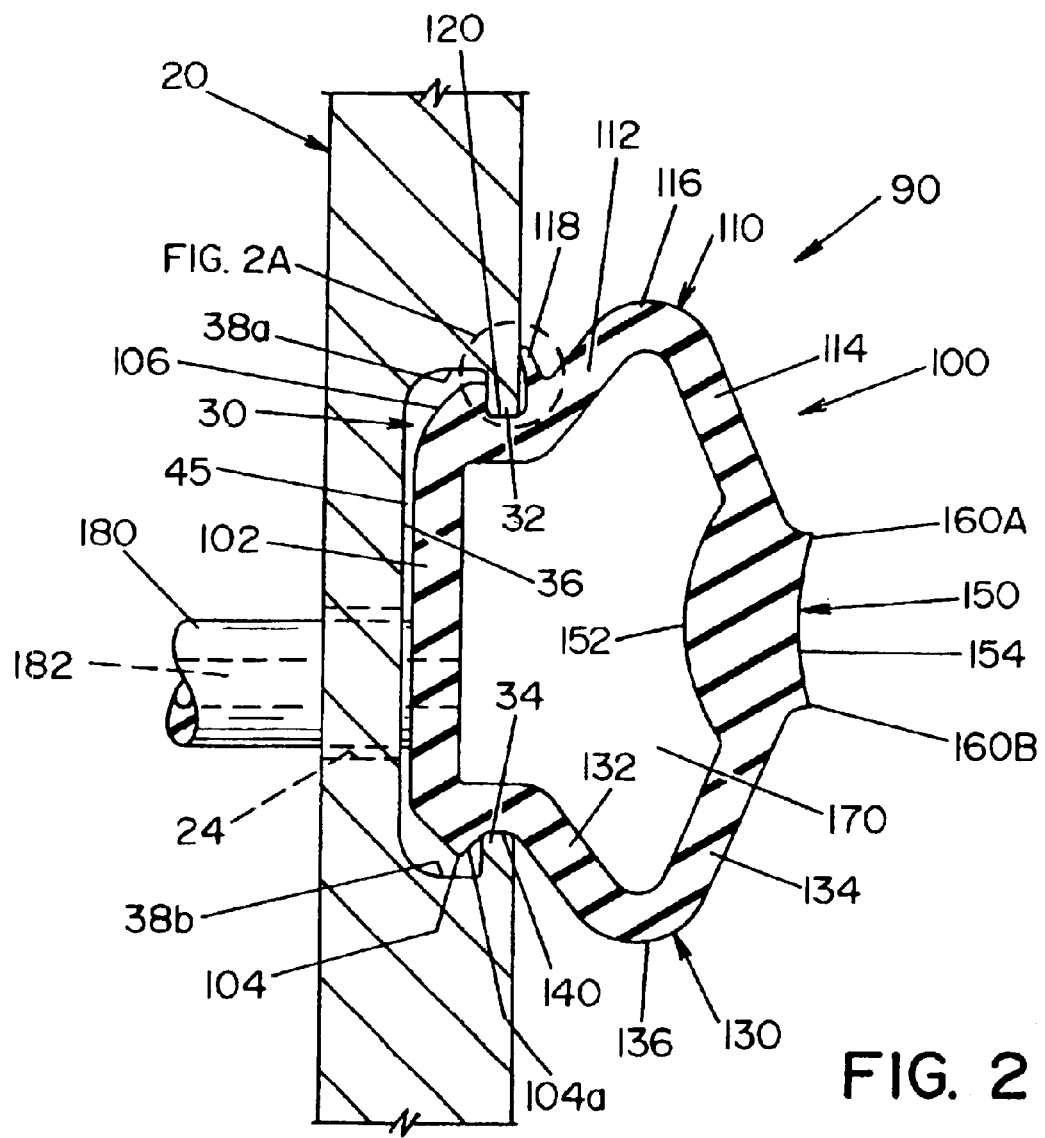
FIG. 2 is a cross-sectional view taken along lines 2—2 of FIG. 1, showing a seal assembly according to a preferred embodiment of the present invention.
Figure 3:
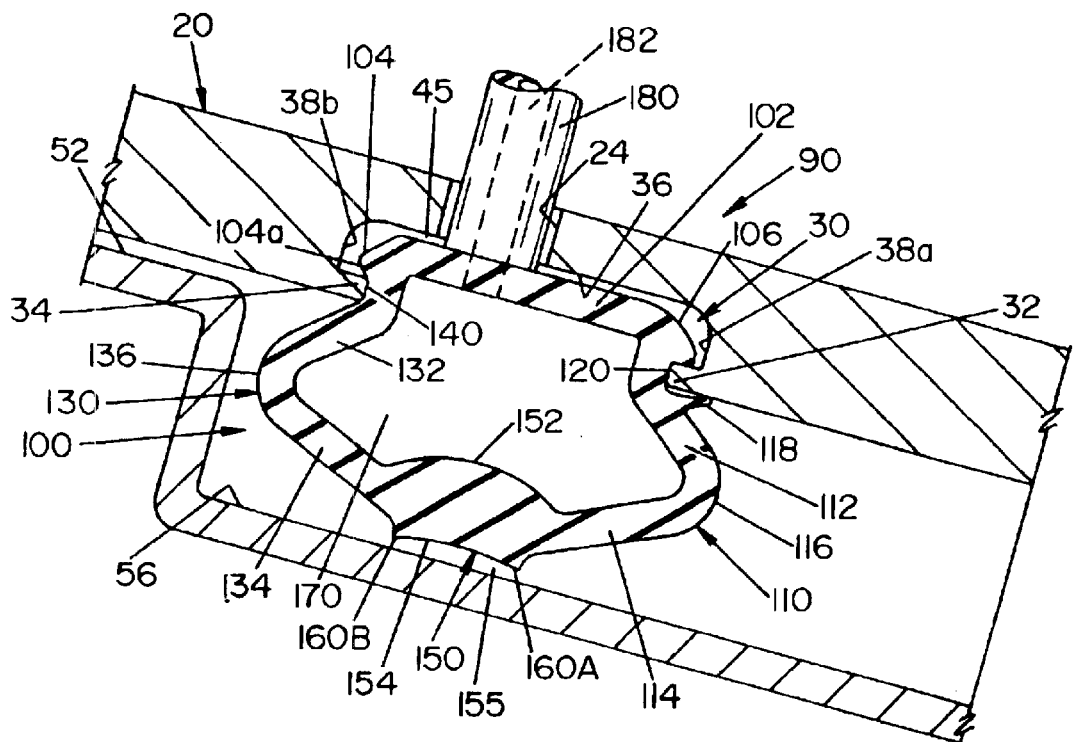
FIG. 3 is a cross-sectional view of the seal assembly with the lid in a closed position.
Figure 4:
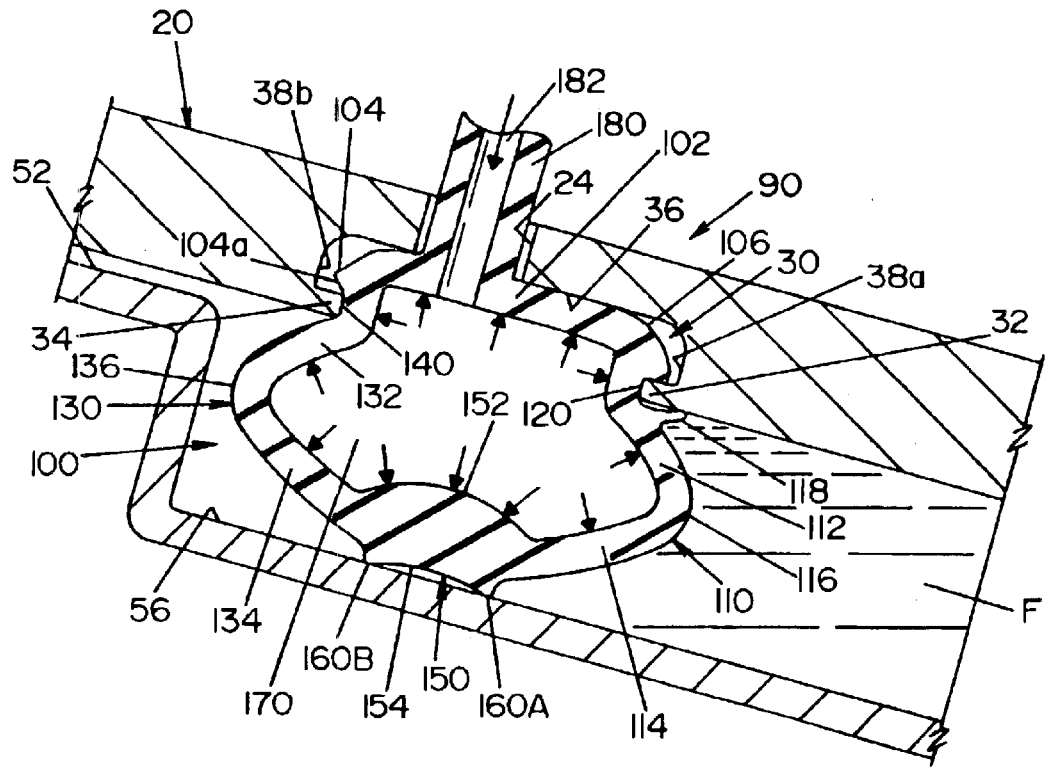
FIG. 4 is a cross-sectional view of the seal assembly in sealing engagement with a housing.

As best seen in FIGS. 2–4, a continuous slot 30 is formed in lid 20, and is dimensioned to receive seal member 100. Slot 30 is defined by a base surface 36, side surfaces 38a, 38b, a square ledge 32, and a rounded ledge 34. Base surface 36 is a generally planar surface. An opening 24 is formed in lid 20 to receive a tube 180 of seal member 100, as will be explained in detail below.

Returning now to FIG. 1, housing 50 includes a generally planar upper surface 52. In the illustrated embodiment, upper surface 52 is sloped. Upper surface 52 includes a generally planar sealing surface 56. In the illustrated embodiment, sealing surface 56 is a shallow depression surrounding the periphery of a cavity 60. A processing chamber is defined by lid 20 and cavity 60.

Cavity 60 is dimensioned to receive one or more articles that are to be decontaminated by exposure to an anti-microbial fluid F. The articles may be placed directly into cavity 60, or arranged in a support structure or container that is located inside cavity 60. Reprocessor 10 is operated to circulate anti-microbial fluid F inside cavity 60, and expose the articles located therein to fluid F, as will be described in greater detail below. Seal assembly 90 (described below) prevents anti-microbial fluid F from escaping the processing chamber, as will be explained below. Locking pins (not shown) lock lid 20 in a closed position, thereby enclosing cavity 60.

It should be understood that automated reprocessor 10 also includes other components for proper operation thereof (e.g., pumps, valves, filter, controller, etc.). However, these components are not described in detail herein, as they are well known to those skilled in the art.

Figure 5:
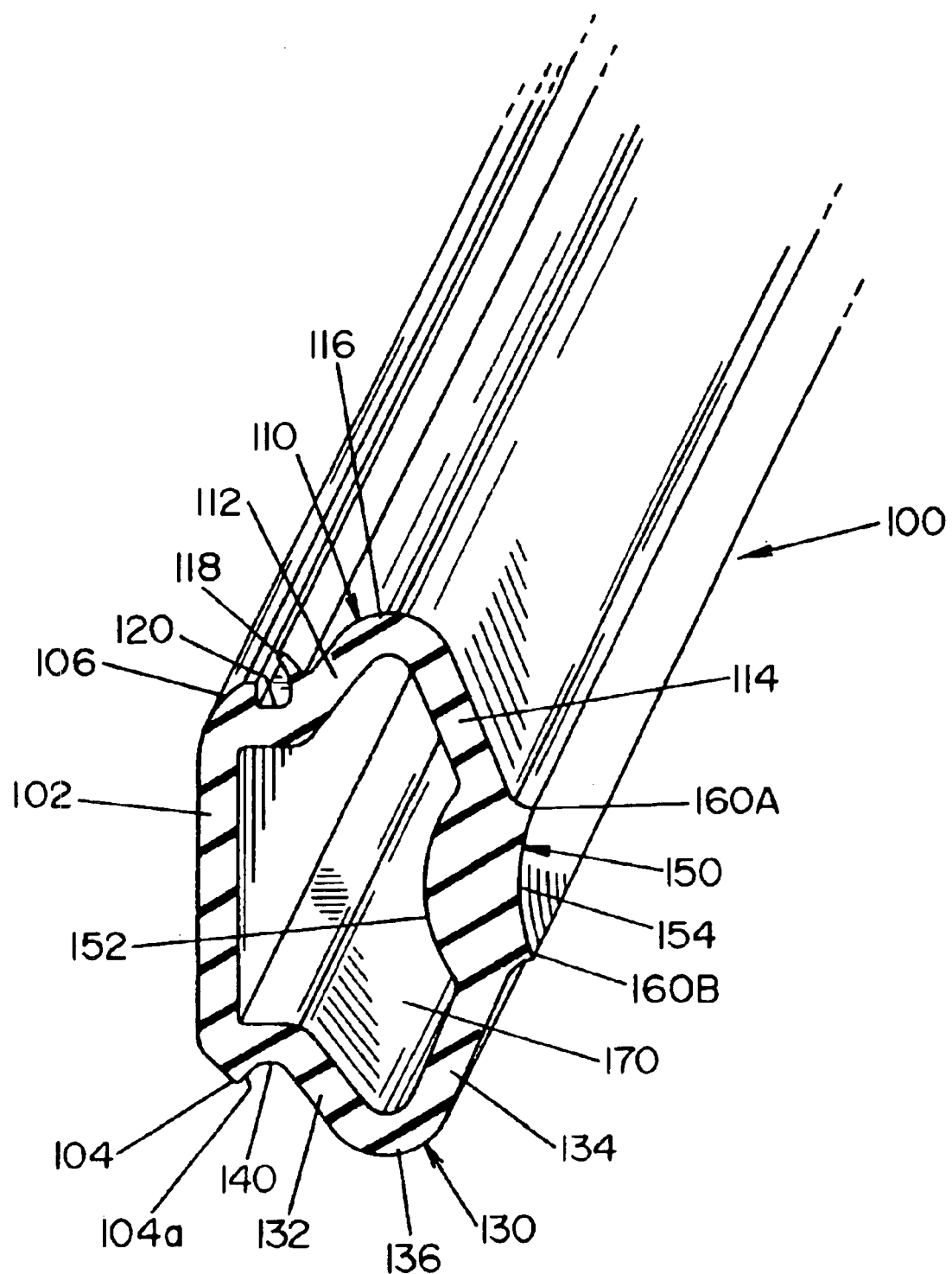
FIG. 5 is a perspective view of the inflatable seal member according to a preferred embodiment of the present invention.

Seal member 100 will now be described in detail with reference to FIG. 5. Seal member 100 is a generally continuous molded element, preferably made of a resilient or flexible material, such as by way of example and not limitation, rubber, polymers, neoprene, natural rubber, butadiene-styrene rubbers, nitrile rubber, cis-1,4 polyisoprene rubber, cis-1,4 polybutadiene rubber, ethylene-propylene rubbers, butyl rubber, chlorosulfonated polyethylenes, polyurethane rubbers, polysulfide rubber and silicon rubbers. Seal member 100 is generally comprised of a generally planar base portion 102, a first V-shaped side wall 110, a second V-shaped side wall 130, and a seal portion 150, that together define an inner cavity 170.

Base portion 102 includes an L-shaped corner 104 and a radiused corner 106. L-shaped corner 104 includes a first surface 104a that is dimensioned to facilitate removal of seal member 100 from slot 30. Radiused corner 106 is dimensioned to facilitate installation of seal member into slot 30. In this regard, radiused corner 106 is to be inserted around lip 32 of slot 30 during installation of seal member 100.

Figure 2A:
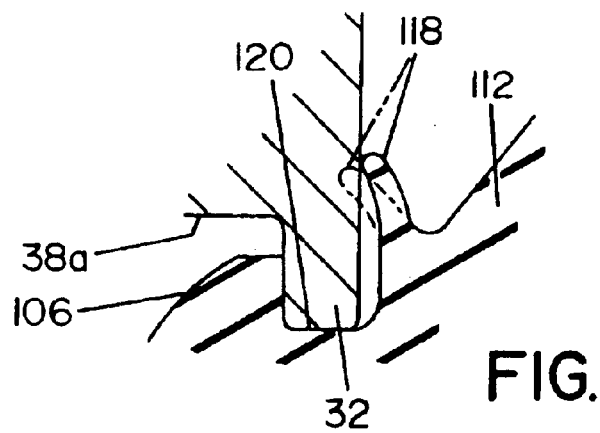
FIG. 2A is an enlarged view of area 2A of FIG. 2.

Side wall 110 is generally comprised of a first wall portion 112 and a second wall portion 114 that are joined at one end to form a corner or joint 116. The other end of wall portion 112 connects with base portion 102, while the other end of wall portion 114 connects with seal portion 150. Corner or joint 116 acts as a hinge, allowing wall portion 112 and wall portion 114 to pivot or flex. A finger 118 is formed along the outer surface of wall portion 112. It should be appreciated that finger 118 is based against lid 20 (FIGS. 2–4). FIG. 2A shows in phantom the normal molded configuration of finger 118. A generally rectangular slot 120, dimensioned to receive ledge 32 of slot 30, is formed between finger 118 and base portion 102 (see FIGS. 2–4).

Side wall 130 is generally comprised of a first wall portion 132 and a second wall portion 134 that are joined at one end to form a corner or joint 136. The other end of wall portion 132 connects with base portion 102, while the other end of wall portion 134 connects with seal portion 150. Corner or joint 136 acts as a hinge, allowing wall portion 132 and wall portion 134 to pivot or flex. A contoured radiused slot 140 receives ledge 34 of slot 30 (see FIGS. 2–4).

Seal portion 150 includes a convex inner surface 152 and an arcuate or concave outer surface 154. As indicated above, seal portion 150 connects with side wall 110 and side wall 130. Outer surface 154 includes a primary sealing edge 160A and secondary sealing edge 160B.

Seal member 100 also includes at least one port that connects with a tube 180. Opening 24 of lid 20 is dimensioned to receive tube 180, as seen in FIGS. 2–4. Tube 180 defines an air channel 182 that is in fluid communication with inner cavity 170 of seal member 100. Air channel 182 allows air to enter and exit inner cavity 170.

As indicated above, seal member 100, together with lid 20, form a seal assembly 90. Seal assembly 90 will now be described in detail with reference to FIGS. 2–4. Seal member 100 is snap-fit into slot 30 formed in lid 20. In this respect, slot 120 of seal member 100 captures a portion of square ledge 32 of lid 20. Furthermore, a portion of seal member 100 surrounds a portion of rounded ledge 34. Accordingly, seal member 100 is secured to lid 20. As discussed above, tube 180 extends through opening 24 of lid 20.

Slot 120 is dimensioned to provide a gap 45 between lid 20 and base portion 102 of seal member 100, when seal member 100 is uninflated.

Finger 118 is based against lid 20 to prevent fluid from entering slot 30 see FIG. 2A). Seal member 100 in the vicinity of radiused corner 106 is dimensioned to abut the inner and edge surfaces of ledge 32, to improve control of deflection of finger 118.

Operation of seal assembly 90 will now be described with reference to FIGS. 1–4. Lid 20 is moveable between an open position (see FIG. 1), wherein cavity 60 is exposed, and a closed position (see FIGS. 3 and 4), wherein cavity 60 is enclosed by lid 20. During a microbial decontamination operation, articles to be decontaminated are placed within cavity 60. Lid 20 is moved from the open position to the closed position to enclose cavity 60. One or more locking pins (not shown) extend from housing 50 to engage with lid 20. The locking pins "lock" lid 20, preventing lid 20 from being moved from the closed position. At the completion of the microbial decontamination operation, the locking pins retract to unlock lid 20, allowing lid 20 to move from the closed position to the open position.

Seal member 100 has two basic configurations, namely, an uninflated normal configuration (FIGS. 2 and 3), and an inflated configuration (FIG. 4). Inner cavity 170 inflates as air is received into inner cavity 170, and deflates as air is released from inner cavity 170.

When lid 20 is in the open position, seal member 100 is in the uninflated normal configuration (FIG. 2). Seal member 100 remains in the uninflated normal configuration when lid 20 is first moved to the closed position shown in FIG. 3. Due to the spacing between lid 20 and sealing surface 56 there is a gap 155 between sealing surface 56 and sealing edges 160A, 160B of uninflated seal member 100. Locking pins extend to lock lid 20 in the closed position. Seal member 100 then assumes the inflated configuration, shown in FIG. 4, as it is inflated by operation of an air source (not shown). In this respect, air is forced through tube 180, and into inner cavity 170, thereby stiffening seal member 100. The air source is operated to maintain the desired pressure.

The air pressure within inner cavity 170 exerts outward forces on the inner surfaces of seal member 100, as illustrated in FIG. 4. The forces applied to seal portion 150 cause outer surface 154 to become less concave (i.e., flattens). Consequently, outer surface 154 moves against sealing surface 56. Accordingly, sealing edges 160A and 160B engage with sealing surface 56. The contact between sealing edges 160A and 160B and sealing surface 56 provide a seal to prevent the release of fluid F from cavity 60. The outward forces on the inner surfaces of seal member 100 also cause base portion 102 to move toward base surface 36, thereby filling gap 45.

During operation of reprocessor 10, fluid F circulates inside cavity 60. Only one side of seal member 100 is exposed to circulating fluid F, as shown in FIG. 4. The outward forces exerted by the air pressure inside inner cavity 170 counteract the forces applied to the outer surfaces of seal member 100 that are exerted by the fluid pressure inside cavity 60. The forces exerted by the fluid pressure further forces finger 118 against the surface of lid 20, thereby improving the sealing effect of finger 118.

When decontamination operations are completed, fluid F circulating in cavity 60 is removed therefrom, and the air is released from inner cavity 170, causing seal member 100 to assume the uninflated normal position (see FIG. 3). After the locking pins are retracted, lid 20 can be moved to an open position (see FIG. 2). The disinfected articles are then removed from cavity 60.

Other modifications and alterations will occur to others upon their and understanding of the specification. It is intended that all such modifications and alterations be included insofar as they come within the scope of the invention as claimed or the equivalents thereof.

Having described the invention, the following is claimed:

1. In a device having a chamber defined by a lid and a cavity, a seal member for sealing the chamber comprising:
   a base portion adapted to be received within a first slot formed in the lid, said base portion having an L-shaped corner at a first end of the base portion and a radiused corner at a second end of the base portion, said L-shaped corner being dimensioned to facilitate removal of said base portion from said first slot, and said radiused corner being dimensioned to facilitate installation of said base portion within said first slot;
   a seal portion having a substantially concave outer surface defining a plurality of sealing edges engageable with a sealing surface surrounding the cavity;
   first and second flexible side walls, each of said first and second flexible side walls connected between the base portion and the seal portion; and
   an inflatable inner cavity defined by the base portion, the seal portion, and the first and second flexible side walls, wherein said first and second flexible side walls flex in response to inflation of the inner cavity to force the plurality of sealing edges into engagement with the sealing surface, said concave outer surface maintaining a concave shape when the inner cavity is inflated.

2. A seal member according to claim 1, wherein each said first and second flexible side walls includes first and second wall portions joined at a corner.

3. A seal member according to claim 1, wherein said seal member further includes at least one port for receiving air into the inflatable inner cavity.

4. A seal member according to claim 3, wherein air pressure inside the inflatable inner cavity exerts forces that counteract external forces on the seal member, thereby maintaining a seal.

5. A seal member according to claim 4, wherein said external forces on the seal member are exerted by fluid pressure inside the chamber.

6. A seal member according to claim 1, wherein said seal member further comprises:
   a second slot formed in said first flexible side wall; and
   a finger extending from said first flexible side wall and biased toward said second slot and engagable with said lid to seal the first slot.

7. In a device having a chamber defined by a lid and a cavity, a seal member for sealing the chamber comprising:
   a base portion adapted to be received within a first slot formed in the lid;
   a seal portion having a substantially concave outer surface defining a plurality of sealing edges engageable with a sealing surface surrounding the cavity;
   first and second flexible side walls, each of said first and second flexible side walls connected between the base portion and the seal portion; and
   an inflatable inner cavity defined by the base portion, the seal portion, and the first and second flexible side walls, wherein said first and second flexible side walls flex in response to inflation of the inner cavity to force the plurality of sealing edges into engagement with the sealing surface, said concave outer surface maintaining a concave shape when the inner cavity is inflated.

8. A seal member according to claim 7, wherein each said first and second flexible side walls includes first and second wall portions joined at a corner.

9. A seal member according to claim 7, wherein said seal member further includes at least one port for receiving air into the inflatable inner cavity.

10. A seal member according to claim 7, wherein air pressure inside the inflatable inner cavity exerts forces that counteract external forces on the seal member, thereby maintaining a seal.

11. A seal member according to claim 7, wherein said external forces on the seal member are exerted by fluid pressure inside the chamber.

* * * * *